(12) United States Patent
Bronstein et al.

(10) Patent No.: US 10,548,502 B2
(45) Date of Patent: Feb. 4, 2020

(54) LOCALIZING ELECTRICAL ACTIVITY IN THE BRAIN USING VIBRATION OF THE CEREBRAL CORTEX

(71) Applicant: RAMOT AT TEL-AVIV UNIVERSITY LTD., Tel Aviv (IL)

(72) Inventors: Alex Bronstein, Haifa (IL); Evgeny Tsizin-Goldman, Ramat Gan (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 16/324,557

(22) PCT Filed: Aug. 21, 2017

(86) PCT No.: PCT/IB2017/055031
§ 371 (c)(1),
(2) Date: Feb. 10, 2019

(87) PCT Pub. No.: WO2018/042282
PCT Pub. Date: Mar. 8, 2018

(65) Prior Publication Data
US 2019/0175044 A1 Jun. 13, 2019

Related U.S. Application Data

(60) Provisional application No. 62/381,031, filed on Aug. 30, 2016.

(51) Int. Cl.
*A61B 5/04* (2006.01)
*A61B 5/0484* (2006.01)
(Continued)

(52) U.S. Cl.
CPC .............. *A61B 5/0484* (2013.01); *A61B 8/00* (2013.01); *A61B 5/6814* (2013.01)

(58) Field of Classification Search
CPC ....... A61B 5/0484; A61B 8/00; A61B 5/0476; A61B 5/7235; A61B 5/0051; A61B 5/04012; A61B 5/6814
See application file for complete search history.

(56) References Cited

U.S. PATENT DOCUMENTS 6,602,202 B2 8/2003 John et al.
8,032,209 B2 * 10/2011 He ..................... A61B 5/04008
600/544
(Continued)

OTHER PUBLICATIONS

Stuart Hameroff, et al., "Transcranial Ultrasound (TUS) Effects on Mental States: A Pilot Study," Brain Stimulation, vol. 6, Issue 3, 2013, pp. 409-415, (Year: 2013).*
(Continued)

*Primary Examiner* — Eric J Messersmith
(74) *Attorney, Agent, or Firm* — Kligler & Associates Patent Attorneys Ltd

(57) ABSTRACT

A diagnostic method includes applying a vibration at a selected frequency to a location within a brain of a living subject (32). Electrical signals resulting from the vibration are measured at multiple positions on a scalp of the subject. The measured electrical signals are processed in order to compute an electrical gain matrix between the location within the brain and the positions on the scalp. Electroencephalogram (EEG) signals are measured at the multiple positions on the scalp. The EEG signals are filtered using the gain matrix in order to identify brain electrical activity originating from the location.

25 Claims, 7 Drawing Sheets

(51) Int. Cl.
*A61B 8/00* (2006.01)
*A61B 5/00* (2006.01)

(56) References Cited

U.S. PATENT DOCUMENTS

| | | | |
|---|---|---|---|
| 2006/0251303 A1 | 11/2006 | He et al. | |
| 2008/0033297 A1 | 2/2008 | Sliwa | |
| 2012/0289869 A1* | 11/2012 | Tyler | A61N 7/00 601/2 |
| 2015/0025409 A1 | 1/2015 | Folkerts et al. | |
| 2015/0151142 A1* | 6/2015 | Tyler | A61B 8/06 601/2 |
| 2016/0213277 A1 | 7/2016 | Wahnoun | |
| 2016/0324437 A1 | 11/2016 | Folkerts et al. | |
| 2017/0080256 A1* | 3/2017 | Kim | A61N 7/00 |

OTHER PUBLICATIONS

Nunez et al., "Electric fields of the brain: the neurophysics of EEG", Oxford University Press, Inc., 2nd edition, New York, USA, pp. 1-626, year 2006.

Hämäläinem et al., "Magnetoencephalography—theory, instrumentation, and applications to noninvasive studies of the working human brain", Reviews of modern Physics, vol. 65, No. 2, The American Physical Society, pp. 413-497, Apr. 1993.

Gramfort et al., "Time-frequency mixed-norm estimates: Sparse M/EEG imaging with non-stationary source activations", NeuroImage ,vol. 70, pp. 410-422, Apr. 15, 2013.

Pascual-Marqui., "Standardized low-resolution brain electromagnetic tomography (sLORETA): technical details", Methods & Findings in Experimental & Clinical Pharmacology 24, Suppl D. pp. 1-16, year 2002.

Helgason et al., "Application of acoustic-electric interaction for neuro-muscular activity mapping: A review", European Journal of Translational Myology—Basic Appl Myol, vol. 24 , No. 4, pp. 261-267, 2015.

Wang et al., "Detection of Multiple Electrical Sources in Tissue Using Ultrasound Current Source Density Imaging", Proceedings of SPIE—The International Society for Optical Engineering, vol. 7629, pp. 1-9, Jun. 11, 2010.

Roth et al., "The movement of a nerve in a magnetic field: application to MRI Lorentz effect imaging", Medical & Biologocal Engineering Computing, vol. 52, No. 5, pp. 491-498, May 1, 2014.

Tse et al., "Conventional and complex modal analyses of a finite element model of human head and neck", Computer Methods in Biomechanics and Biomedical Engineering , vol. 18, issue 9, pp. 961-973, year 2015.

Fatemi et al., "Vibro-acoustography: An imaging modality based on ultrasound-stimulated acoustic emission", Proceedings of the National Academy of Sciences, vol. 96, issue 12, pp. 6603-6608, Jun. 1999.

Beyer et al., "Radiation pressure—the history of a mislabeled tensor", The Journal of the Acoustical Society of America, vol. 63, issue 4, pp. 1025-1030, Apr. 4, 1978.

Konofagou et al., "Localized harmonic motion imaging: theory, simulations and experiments", Ultrasound in medicine & biology. vol. 29, issue 10, pp. 1405-1413, Apr. 8, 2003.

McDannold et al., "Transcranial MRI-guided focused ultrasound surgery of brain tumors: Initial findings in three patients", Neurosurgery, vol. 66., issue 2, pp. 323-332, Feb. 2010.

Destrieux et al., "Automatic parcellation of human cortical gyri and sulci using standard anatomical nomenclature", Neuroimage, vol. 53, No. 1, pp. 1-15, Oct. 15, 2010.

Evans et al., "3D statistical neuroanatomical models from 305 MRI volumes", Nuclear Science Symposium and Medical Imaging Conference, International Corporation, IEEE Conference Record, pp. 1813-1817, year 1994.

Tadel et al., "Brainstorm: a user-friendly application for MEG/EEG analysis", Computational intelligence and neuroscience, Hindawi Publishing Corporation, vol. 2011, pp. 1-13, year 2011.

Dassault Systemes, "Abaqus 2010—Abaqus analysis user's manual", vol. III: Materials, pp. 1-679, year 2010.

Sack et al., "The impact of aging and gender on brain viscoelasticity", Neuroimage , vol. 46, issue 3, pp. 652-657, Mar. 10, 2009.

Kruse et al., "Magnetic Resonance Elastography of the Brain", Neuroimage, vol. 39, issue 1, pp. 231-237, Jan. 1, 2008.

Min et al., "Focused ultrasound-mediated suppression of chemically-induced acute epileptic EEG activity", BMC Neuroscience, vol. 12.1, issue 23, pp. 23, pp. 1-12, 2011.

Legon et al., "Transcranial focused ultrasound modulates the activity of primary somatosensory cortex in humans", Nature Neuroscience, vol. 17, No. 2, pp. 322-329, Feb. 2014.

Roth et al., "A theoretical model for magneto-acoustic imaging of bioelectric currents", IEEE Transactions on Biomedical Engineering, vol. 41 ,Issue 8 , p. 723-728, Aug. 1994.

International Application # PCT/IB2017/055031 search report dated Dec. 4, 2017.

Mariappan et al., "Magnetic Resonance Elastography: A Review", Clinical Anatomy, vol. 23, issue 5, pp. 497-511, Jul. 2010.

* cited by examiner

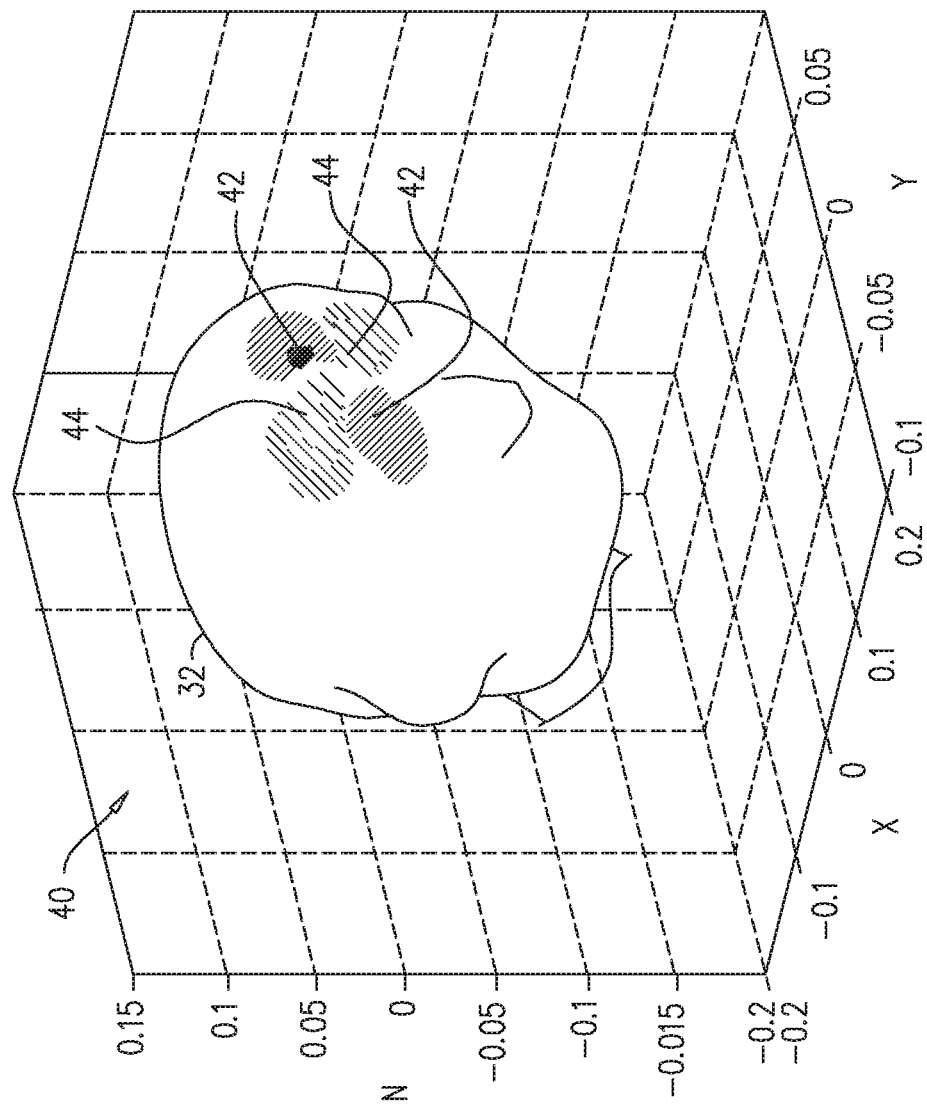

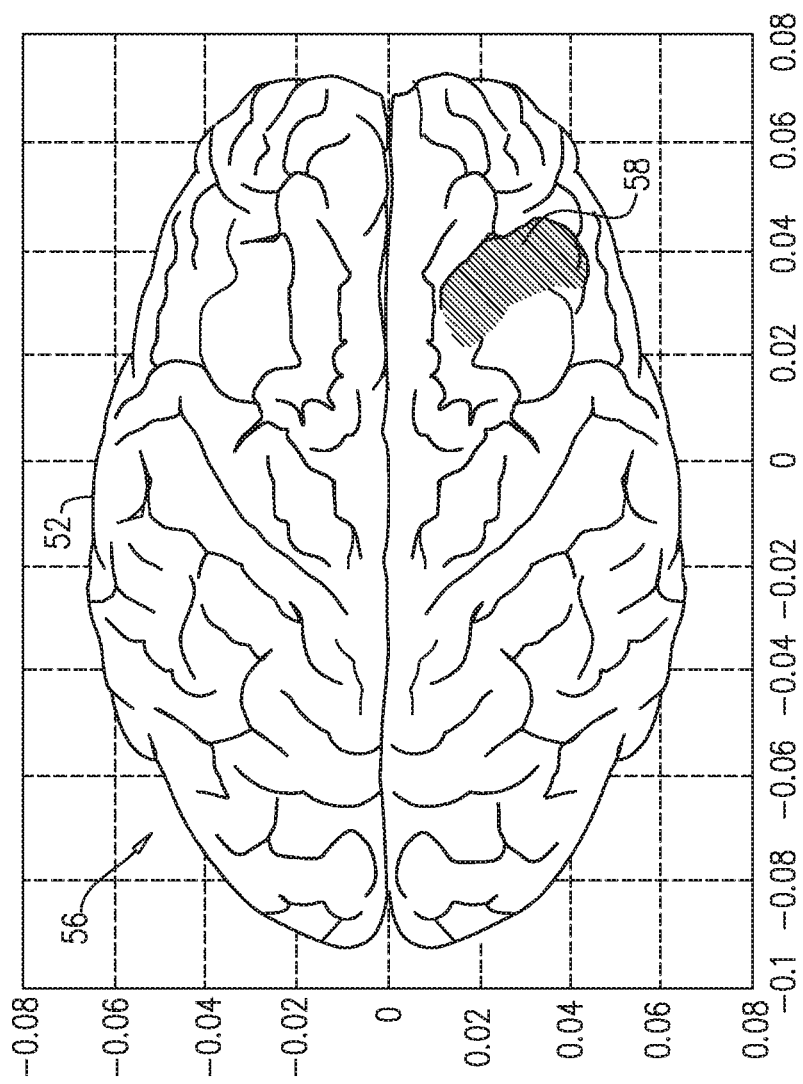

ID
LOCALIZING ELECTRICAL ACTIVITY IN THE BRAIN USING VIBRATION OF THE CEREBRAL CORTEX

CROSS-REFERENCE TO RELATED APPLICATION

This application claims the benefit of U.S. Provisional Patent Application 62/381,031, filed Aug. 30, 2016, which is incorporated herein by reference.

FIELD OF THE INVENTION

The present invention relates generally to medical imaging, and specifically to techniques for functional imaging of brain activity.

BACKGROUND

Electroencephalography (EEG) is a noninvasive measurement technique of the electrical potentials over the scalp, aiming to reconstruct the underlying primal electrical activity of the brain cortex. Due to the high temporal resolution of EEG, it is a valuable tool both for diagnosis of neural diseases (epilepsy being a well-known example) and for research.

On the other hand, conventional EEG measurement is capable of only low spatial resolution. One reason for this low spatial resolution is the unsolved complexity of electrical conductivity distribution within the head. Another reason is the influence of the skull on the propagation of the electrical signal from the neural sources to the scalp: The skull effectively acts as a spatial low-pass filter. This limitation restricts the number of meaningful EEG electrodes that can be distributed over the skull to about 200, which is much lower than the number of possible neural sources (about 10,000). This enormous difference between neural sources and effective measurement points makes the process of reconstruction of the cortical electrical activity from the EEG measurements severely ill-posed. The complexity of the cortical activations also gives rise to electrical noise, which can bury the electrical activity of interest and requires extensive averaging to overcome.

Recently, a number of techniques have emerged that intentionally perturb the electrical signal resulting from cortical activity, with the aim of improving the reconstruction process. For example, Helgason et al. describe an acousto-electric technique (AET) for current density imaging in "Application of acoustic-electric interaction for neuro-muscular activity mapping: A review," *European Journal of Translational Myology* 24:4 (2015). In this technique, focused ultrasound is used to perturb locally the conductivity of the neural medium, giving potentially new information on the EEG signal.

As another example, Roth et al. describe magneto-acoustic imaging (MAI) of bioelectric currents in "The movement of a nerve in a magnetic field: application to MRI Lorentz effect imaging," *Medical & biological engineering & computing* 52:5 (2014), pages 491-498. The goal in this technique is to measure the neural activity directly, employing the Lorentz force originating due to the magnetic field at the location of the electrical activity. This force induces the motion of the tissue that could be measured either by MRI or by measuring the acoustic field it induces.

SUMMARY

Embodiments of the present invention that are described herein provide improved systems and signal processing techniques for EEG-based mapping and diagnosis.

There is therefore provided, in accordance with an embodiment of the invention, a diagnostic method, which includes applying a vibration at a selected frequency to a location within a brain of a living subject. Electrical signals resulting from the vibration are measured at multiple positions on a scalp of the subject. The measured electrical signals are processed in order to compute an electrical gain matrix between the location within the brain and the positions on the scalp. Electroencephalogram (EEG) signals are measured at the multiple positions on the scalp. The EEG signals are filtered using the gain matrix in order to identify brain electrical activity originating from the location.

In some embodiments, measuring the electrical signals includes extracting the electrical signals at the frequency of the vibration. Typically the frequency of the vibration is in a first range between 100 Hz and 10,000 Hz, while the EEG signals are measured in a second range, which is below 100 Hz.

Additionally or alternatively, applying the vibration includes applying vibrations to multiple different locations within the brain, in order to compute respective gain matrices for the locations, and filtering the EEG signals includes constructing a map of the brain electrical activity over the multiple different locations using the gain matrices.

Further additionally or alternatively, applying the vibration includes applying vibrations at multiple different frequencies so as to excite multiple different vibrational modes in different locations in the brain, and processing the measured electrical signals includes computing respective electrical gain matrices corresponding to the different vibrational modes. In one embodiment, filtering the EEG signals includes distinguishing between the EEG signals arising from mutually-adjacent locations on different sulci of the brain, which are excited by different ones of the vibrational modes. Additionally or alternatively, filtering the EEG signals includes concatenating the electrical gain matrices to produce a combined gain matrix, inverting the combined gain matrix, and applying the inverted gain matrix to the EEG signals in order to reconstruct the electrical activity in the brain.

In some embodiments, applying the vibration includes directing ultrasonic waves toward the brain at different, first and second ultrasonic frequencies, which are separated by a frequency difference equal to the selected frequency of the vibration. In a disclosed embodiment, applying the vibration includes focusing the ultrasonic waves onto the location within the brain.

There is also provided, in accordance with an embodiment of the invention, a diagnostic system, including one or more acoustic transducers, which are configured to apply a vibration at a selected frequency to a location within a brain of a living subject. An array of electrodes are configured to measure electrical signals resulting from the vibration at multiple positions on a scalp of the subject and to measure electroencephalogram (EEG) signals at the multiple positions on the scalp. A console is configured to process the measured electrical signals in order to compute an electrical gain matrix between the location within the brain and the positions on the scalp, and to filter the EEG signals using the gain matrix in order to identify brain electrical activity originating from the location.

There is additionally provided, in accordance with an embodiment of the invention, a diagnostic method, which includes identifying a resonant frequency of vibration of a part of an organ in a body of a living subject. Acoustic energy is applied at the identified resonant frequency to the body in a vicinity of the organ. A characteristic of electrical signals resulting from the vibration in response to the applied acoustic energy is measured at one or more positions on a surface of the body.

In one embodiment, identifying the resonant frequency includes processing a volumetric image of the organ in order to estimate a frequency response of the organ. Additionally or alternatively, identifying the resonant frequency includes measuring the resonant frequency using magnetic resonance elastography. Further additionally or alternatively, identifying the resonant frequency includes applying the acoustic energy to the body at multiple different frequencies, and measuring a response of the organ so as to identify a resonant response.

In some embodiments, measuring the characteristic of the electrical signals includes extracting the electrical signals at the resonant frequency of the vibration. Extracting the electrical signals can include measuring the electrical signals in a combination of resonant modes.

Additionally or alternatively, applying the acoustic energy includes applying vibrations to multiple different locations within the organ, and measuring the characteristic of the electrical signals includes constructing a map of electrical activity over the multiple different locations. In some embodiments, applying the vibrations includes exciting multiple different vibrational modes in different locations in the organ. In a disclosed embodiment, the organ is the brain, and constructing the map includes distinguishing between the electrical signals arising from mutually-adjacent locations on different sulci of the brain, which are excited by different ones of the vibrational modes.

There is further provided, in accordance with an embodiment of the invention, a diagnostic system, including one or more acoustic transducers, which are configured to apply acoustic energy to a body of a living subject in a vicinity of an organ in the body at a resonant frequency of vibration of a part of the organ. One or more electrodes are configured to measure a characteristic of electrical signals resulting from the vibration in response to the applied acoustic energy at one or more positions on a surface of the body. A console is configured to process the measured characteristic in order to analyze electrical activity originating from the organ.

The present invention will be more fully understood from the following detailed description of the embodiments thereof, taken together with the drawings in which:

BRIEF DESCRIPTION OF THE DRAWINGS

FIGS. 2A and 2B are schematic maps of vibroEEG signals due to acoustic stimulation at two different locations within the brain, in accordance with an embodiment of the invention;

FIGS. 3A and 3B are schematic maps of vibroEEG signals due to acoustic stimulation of two different vibrational modes in the brain, in accordance with an embodiment of the invention;

DETAILED DESCRIPTION OF EMBODIMENTS

Overview

Figure 1:
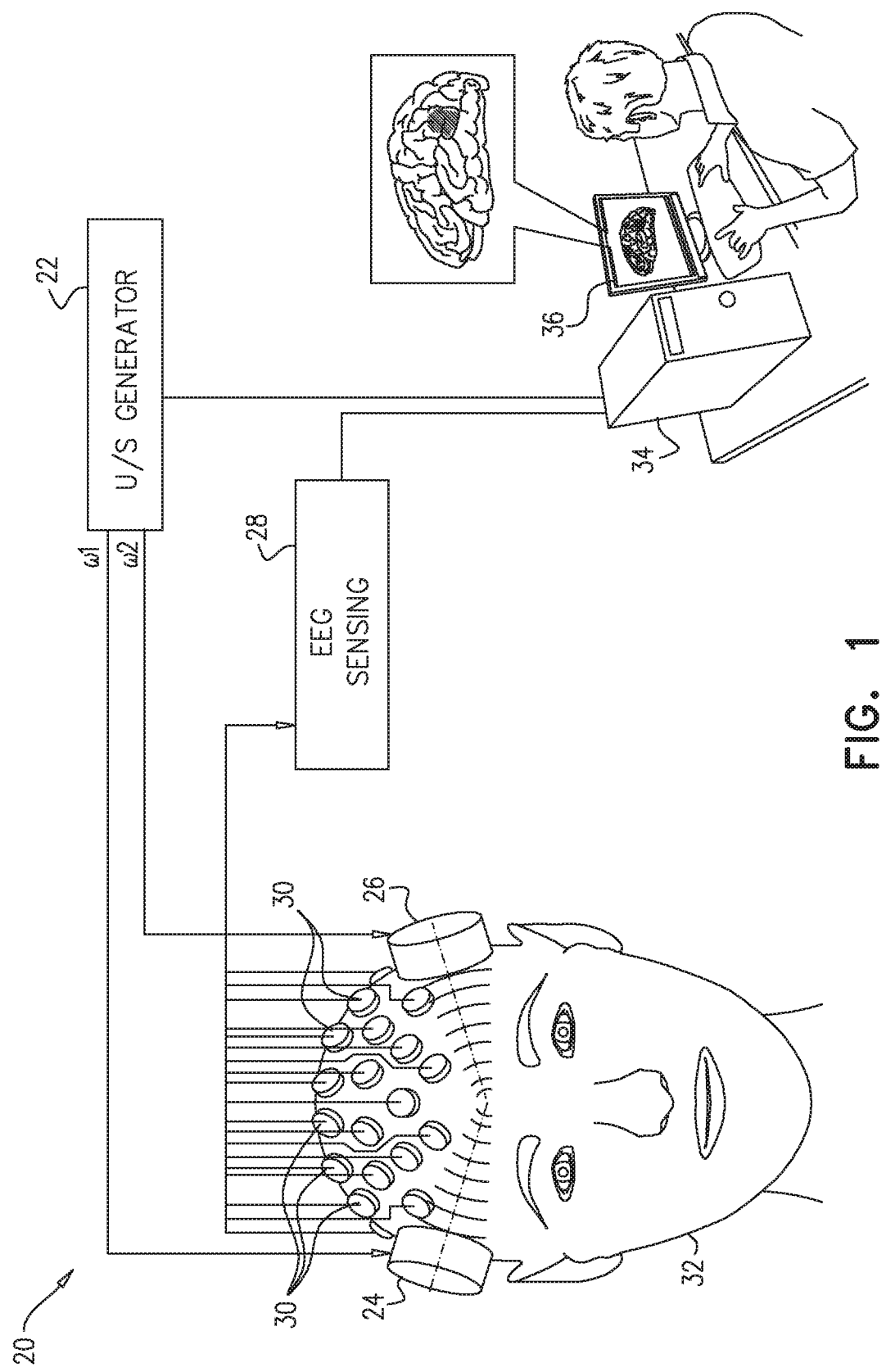
FIG. 1 is block diagram that schematically illustrates a system for vibroEEG measurement and processing, in accordance with an embodiment of the invention.

Embodiments of the present invention that are described herein provide new systems and signal processing techniques that improve substantially the spatial resolution of EEG, and thus enhance the diagnostic and research value of EEG measurements.

The disclosed techniques are referred to herein as "vibroEEG." These techniques operate by exciting vibrational modes of the electrically-active brain cortex and recording the narrowband electrical signal on the scalp resulting due to the oscillating neural source. They take advantage of the fact that the cerebral cortex has resonant modes on the order of hundreds of Hertz, which can be generated locally and controllably (as described, for example, by Konofagou et al., in "Localized harmonic motion imaging: theory, simulations and experiments," *Ultrasound in medicine & biology* 29:10 (2003), pages 1405-1413.) This frequency range is sufficiently low to generate displacements of the cortex large enough to create measurable signals without leading to high stresses and dissipated power within the tissue, but high enough so as not to interfere with the EEG frequency range of about 0-100 Hz. This arrangement permits probing the neural activity locally both in space and in time, with high signal/noise ratio (SNR) due to the concentration on both the narrowband signal of the vibroEEG and the localized region of the cortex.

In the disclosed embodiments, acoustic transducers excite vibrational modes of the electrically-active brain cortex, and an EEG system records the distinct electrical potentials on the scalp that result from the oscillating neural source. Thus, instead of applying an ill-posed model (mixing in every electrode the electrical activity of many sources), the present embodiments essentially probe the neural activity in the specific vibrating location. Using the electrical response of the cerebral cortex to multiple different patterns of vibration, the gain matrix—which relates the electrical signals measured on the scalp to the actual electrical activity in the brain—is enriched with new independent equations, making the process of reconstruction much more efficient.

In some embodiments of the present invention, ultrasonic transducers apply a vibration at a selected frequency to a location within the brain of a living subject. Low-frequency local tissue oscillation (for example, with frequencies in the desired range of hundreds of Hertz) can be induced by mixing of localized high-frequency pressure waves at different frequencies. An EEG system measures the electrical signals resulting from the vibration at multiple positions on the subject's scalp. A computer processes these electrical signals in order to compute an electrical gain matrix between the vibrating location within the brain and the positions on the scalp. (In particular, the computer can extract and process the electrical signals in a narrow band at the specific frequency of vibration.) The gain matrix that is computed in this manner can then be used in filtering EEG signals measured at these same positions on the scalp in order to identify brain electrical activity originating from the location in question.

In computing the gain matrix, the "resting state" cortical electrical activity is utilized. As is known from studies using depth electrodes, the resting state cortical activity has similar amplitudes in different parts of the cortex. Although there is still some variability among different areas of the cortex, it is at least an order of magnitude lower than the currents of the activated areas of the brain. Accordingly, the gain vector (the column of the gain matrix corresponding to a certain location on the cortex) calculated from the vibrating "resting" part of the cortex for each location is calculated up to some multiplicative constant. (The distribution of the gain vector over the scalp is calculated precisely, but since the value of the resting state activity can only be estimated, the energy of the gain vector corresponding to the given source is known approximately.) This variability will not influence the localization accuracy of the activated areas, but it can influence the power estimation of the reconstructed activation.

For key clinical applications of the present embodiments (for instance, in diagnosis of epilepsy), the approximation used in computation of the gain matrix will have little effect, since the electrical activity of the activated zones is orders of magnitude higher than the resting state activity. In some cases, however (such as modeling of the EEG gain matrix), the approximation will affect both the localization and the power estimation accuracy.

In some embodiments, the present techniques are applied in mapping electrical activity within the brain. For this purpose, acoustic vibrations can be applied to multiple different locations in the brain, thus enabling the computer to compute respective gain matrices for the locations. The EEG signals can then be filtered using these gain matrices in order to construct a map of the brain's electrical activity. Additionally or alternatively, the vibrations can be applied at multiple different frequencies so as to excite multiple different vibrational modes in different locations in the brain, whereby the computer is able to compute and apply respective electrical gain matrices corresponding to the different vibrational modes.

Using the present techniques, neural activity can effectively be probed directly in any location in the head. In one example, the disclosed techniques are used in resolving closely-spaced deep neural sources on different cortical sulci, which are non-separable using conventional EEG. While close together in Euclidian terms, these sources are distant with respect to the intrinsic geometry of the cortex. As a result the sources are stimulated in different vibrational modes and can be discriminated using vibroEEG. Thus, the intrinsic geometry of the cortex is used to improve the localization accuracy of neural sources.

System Description

FIG. 1 is block diagram that schematically illustrates a system 20 for vibroEEG measurement and processing, in accordance with an embodiment of the invention. System 20 comprises an ultrasound generator 22, which drives two or more acoustic transducers 24, 26 to emit ultrasonic waves into a head 32 of a patient. Transducers 24 and 26 are typically driven at different frequencies, $\omega_1$ and $\omega_2$, which are chosen so that the desired acoustic excitation frequency $\Delta\omega$ at target locations in the patient's brain is equal to the frequency difference $\Delta\omega = \omega_1 - \omega_2$. To excite specific target locations within head 32, transducers 24, 26 may comprise directional emitters, such as one or more phased arrays, which can be aimed to focus ultrasonic waves toward the target locations.

Ultrasound generator 22 and transducers 24, 26 may comprise any suitable sorts of such devices that are known in the art. For example, the Exablate Neuro system produced by Insightec Ltd. (Tirat Hacarmel, Israel) includes an array of transducers that can be adapted to generate focused ultrasonic pressure within the brain at the appropriate frequencies. Alternative, a single acoustic transducer can be sufficient for some embodiments of the present invention. To reduce electrical noise in the EEG measurements, the ultrasonic waves can be delivered to the head through acoustic waveguides, rather than by direct application as shown in FIG. 1.

An EEG front end 28 senses, amplifies, filters, and digitizes electrical signals from an array of electrodes 30 that are placed at respective sensing locations in contact with the scalp of head 32. Electrodes 30 and front end 28 are capable of sensing both conventional EEG frequencies (typically up to about 100 Hz) and vibroEEG frequencies in the range of 100-10,000 Hz. Standard EEG electrodes and EEG measurement systems that are known in the art may be used for this purpose, although it is desirable that the bandwidth of the EEG input circuits be increased in order to measure the higher-frequency vibroEEG signals.

A console 34 drives ultrasound generator 22 at the desired frequencies and receives the digitized signals from EEG front end 28. Based on the selected excitation frequency $\Delta\omega$ (or frequencies) and the corresponding input from front end 28, console 34 measures the vibroEEG signal at the selected excitation frequencies for each target location in the brain. On this basis, console 34 computes a respective gain matrix for each location and each excitation frequency. The console uses these gain matrices in filtering natural EEG signals that it receives from front end 28 in the absence of vibrational excitation of the brain, in order to localize and map the EEG activity. Console 34 outputs the results of this processing, for example to a display 36, which graphically illustrates the amplitude distribution and other features of electrical activity in the brain.

Typically, console 34 comprises a general-purpose computer, which has suitable interfaces for communication with the other elements of system 20 and is programmed in software to carry out the functions that are described herein. This software may be stored, for example, on tangible, non-transitory computer-readable media, such as optical, magnetic, or electronic memory media. Alternatively, at least some of the functions of console 34 may be carried out in hard-wired or programmable logic.

Theory of Operation

The Forward and Inverse EEG Problems

The EEG is produced mainly by the electrical activity of the pyramidal neurons within the cerebral cortex. These neurons are directed normal to the cortex and are commonly activated synchronously by groups of tens of thousands of neurons. This synchronous activity generates electrical potentials on the scalp, which are measured as EEG.

The local cortical electrical activation is usually modeled as a current dipole, while on the macro scale the head is modeled as consisting of regions of constant electrical conductivity $\sigma$. It can be shown that within a quasi-static approximation that is valid for the frequencies of interest, the primary current distribution $J^P(r)$ gives rise to an electrical potential $V(r)$ according to Poisson's equation and to a magnetic field according to the law of Biot-Savart:

$$\nabla \cdot (\sigma \nabla V) = \nabla \cdot J^P(r)$$

$$B(r) = \frac{\mu_0}{4\pi} \int (J^P(r') + V(r')\nabla'\sigma) X \frac{(r-r')}{|r-r'|^3} dv'$$

Consider now a discretized geometry with S possible locations of electrical sources $x_1, \ldots, x_S$ and N possible locations of electrodes $r_1, \ldots, r_N$, where the resulting electrical potentials are measured. We assume the current dipoles are perpendicular to the cortex and note that the linearity of Poisson's equation implies existence of a gain matrix $G \in R^N$ connecting the cortical signal vector $x \in R^S$ with the vector of measured potentials $M \in R^N$. Taking into consideration the measurement noise $E \in R^N$, we can write:

$$M = GX + E$$

To find the gain matrix G, console 34 solves the EEG forward problem relating the distribution of the electrical potentials M on the scalp of head 32 to a given distribution of the electrical conductivity within the head and the primary current sources X (assuming that X is known). The inverse EEG problem is the problem of finding the distribution of current sources from the measurements on the scalp. For real values of the electrical conductivity distribution within the head, the potential on the scalp is smooth, and the number of electrodes 30 sufficient to represent it reliably is about 100. The number of possible source positions within head 32, however, is about 10,000 (taking into consideration that the minimal electrically-active element of cortex that can be measurable on the EEG is about 1 cm$^2$).

Accordingly, in the absence of vibroEEG measurements, there are an infinite number of possible solutions to the EEG inverse problem.

Vibrational Analysis of the Human Cortex

Console 34 uses the vibration of the human cortex, induced by transducers 24 and 26, in order to improve the EEG inverse problem solution. For this purpose, we assume that the geometry of the brain is discretized into $N_e$ elements. For such a discretized linear mechanical vibrating system, the following equation can be written:

$$[M]\{\ddot{x}\} + [C]\{\dot{x}\} + [K]\{x\} = \{f\}$$

wherein [M], [C], and [K] are symmetric $N_e \times N_e$ matrices, referred to respectively as the mass, damping, and stiffness matrices. These matrices characterize the mechanical properties of the system.

Consider now undamped free vibrations with frequency $\omega$:

$$(-\omega^2[M] + [K])\{\tilde{X}\}e^{i\omega t} = 0$$

The resonant frequencies of vibration correspond to the solutions of the equation:

$$-\omega^2[M] + [K] = 0$$

For the general case of the harmonic force $\{f(t)\} = \{\tilde{F}\}e^{i\omega t}$, the steady state solution is given by:

$$(\omega^2[M] + \omega[C] + [K])\{\tilde{X}\} = \{\tilde{F}\}$$

$$\{\tilde{X}\} = (\omega^2[M] + \omega[C] + [K])^{-1}\{\tilde{F}\}$$

Assuming the damping-related term $\omega[C]$ to be small, the amplitude of vibration of each mechanical element will be high near its resonant frequencies. For a system made up of independent blocks, the resonances of these blocks can be calculated independently. Research has shown that this is a reasonable assumption with respect to the cerebral cortex. Furthermore, the folded structure of the cortex (comprising gyri and sulci, referring to convex and concave folds relative to the center of head 32) supports the added simplification that vibrations of different sulci are largely independent when local harmonic force is applied. The above simplifications can be applied, for example, in order to reduce the computational burden of the calculation vibrational modes of different folds of the cerebral cortex.

Acoustic Field Generation

As shown in FIG. 1, transducers 24 and 26 generate respective ultrasonic beams with slightly different frequencies $\omega_1$, $\omega_2$, intersecting in a focal region. This intersection creates an amplitude-modulated acoustic wave:

$$P(t) = P_0 \cos\left(\frac{\omega_1 - \omega_2}{2}t\right)\cos\left(\frac{\omega_1 + \omega_2}{2}t\right) = P_0 \cos\left(\frac{\Delta\omega}{2}t\right)\cos(\omega_0 t),$$

$$\Delta\omega \ll \omega_0$$

wherein $\omega_0 = \omega_1 + \omega_2$.

The pressure of the acoustic wave produces radiation force F that is proportional to the energy density of the incident acoustic wave <E>, the projected area of the target object S, and the drag coefficient $d_r$, which results from the scattering and absorbing properties of the irradiated object: $F = S<E>d_r$. The energy density is given by:

$$\langle E \rangle = \frac{P^2(t)}{\rho c^2}$$

wherein $\rho$ and c are the density and propagation speed, respectively, of the acoustic waves in the medium.

The time-averaged force over a period of time T that satisfies $$\Delta\omega \ll \frac{2\pi}{T} \gg \omega_0$$

has an alternating part that changes at the difference frequency $\Delta\omega$:

$$\langle F \rangle_T = \frac{1}{2T}\int_{t+T}^{t-T} F = \frac{P_0^2 S}{4\rho c^2}d_r(1 + \cos\Delta\omega t)$$

Thus, acoustic excitation by transducers 24 and 26 creates a local low-frequency force in a region much smaller than the corresponding wavelength. The frequency of the force can be chosen to be equal to one of the resonant frequencies of the cortex that has a high response in the target location where the force is applied. This force in turn induces a high-amplitude periodic narrowband localized displacement of the brain tissue. The actual amplitude of the displacement can be measured, for instance using the technique described by Fatemi et al., in "Vibro-acoustography: An imaging modality based on ultrasound-stimulated acoustic emission," *Proceedings of the National Academy of Sciences* 96:12 (1999), pages 6603-6608.

VibroEEG

The vibroEEG signal is defined as the change of the measured EEG signal due to vibration of the electrically active cortex. Let us denote by the function G (r, r') the solution of the EEG forward problem at point r due to the unit current dipole placed perpendicular to the cortex at point r'. In view of the linearity and the spatial invariance of Poisson's equation, the change of the EEG due to the small displacement of the source will be given by the scalar product of the gradient of G(r,r') with the displacement vector d(r'). Accordingly, for the distribution of the displacement over the cortex $d(r_c)$ and the electrical cortical activity $x(r_c)$, the resulting vibroEEG signal will be:

$$V(r) = \int_{cortex} \nabla' G(r,r') \cdot d(r') x(r') dA'$$

Whereas the EEG signal is the potential of current dipoles, the vibroEEG signal involves the gradient of the current dipole field, which is essentially the field of the current quadrupoles. This point is useful in solving the inverse problem, because the field of current quadrupoles is sharper than that of the current dipoles.

The displacement frequency response of the cortex to the unit-magnitude single-frequency point pressure field $P_{unit} = \hat{n}_p \delta(r - r_c) e^{j\omega t}$ is given by the scalar product:

$$\hat{d}(r,\omega) = \hat{n}_p \cdot A(r,r_c,\omega)$$

In this formula, $n_p$ is a unit vector, $\delta$ is the Dirac delta function, and $A(r,r_c,\omega)$ is the influence function connecting the vibration (amplitudes and phases of the displacements in the x-, y- and z-directions) at point r to unit omnidirectional vibration at point $r_c$ at frequency $\omega$. For a general pressure field distribution, the displacement as a function of location and frequency can be calculated using the integral:

$$d(r,\omega) = \int_{r' \in cortex} P(r',\omega) \cdot A(r,r',\omega) dA$$

Substituting this expression for the local, frequency-dependent displacement into the above formula for the vibroEEG, and assuming constant activations x(r), gives the general formula:

$$V(r,\omega) = \int_{r' \in cortex} \nabla' G(r,r') \cdot x(r') \left( \int_{r'' \in cortex} P(r'',\omega) \cdot A(r',r'') dA'' \right) dA'$$

Restriction of the points where the signal is measured to the locations of electrodes 30, $r_1, \ldots, r_N$, gives the gain matrix G for the vibroEEG signal.

Console 34 computes and applies this vibroEEG signal as the input to the inverse problem of electrical activity reconstruction. The vibroEEG inverse problem has a new dimension of frequency, corresponding to the frequency or frequencies of acoustic stimulation of the cortex. Using a discrete set of frequencies $\omega_1, \ldots, \omega_{N_f}$, with a corresponding distribution of pressure fields localized on the folds of the cortex, will give $N_f$ vibroEEG measurements and $N_f$ gain matrices $G_1, \ldots, G_{N_f}$, corresponding to different frequencies. Concatenating these measurements gives $N_f$ equations corresponding to the EEG inverse problem, thus reducing the ill-posedness of the problem:

$$\begin{bmatrix} M_1 \\ \vdots \\ M_{N_f} \end{bmatrix} = \begin{bmatrix} G_1 \\ \vdots \\ G_{N_f} \end{bmatrix} X + \begin{bmatrix} E_1 \\ \vdots \\ E_{N_f} \end{bmatrix}$$

By measuring EEG signals at multiple different acoustic stimulation frequencies, the rank of the vibroEEG gain matrix that is constructed in this manner can be made substantially higher than the rank of the original EEG matrix. Thus, console 34 can invert the gain matrix without dependence on regularization, and thus provide a reliable filter for mapping natural EEG signals back to their locations of origin in the brain.

Moreover, as noted earlier, for localized oscillations, such as oscillations of different sulci at different resonant frequencies, the activations of the different sulci can be probed directly, leading to an uncoupled inverse problem for each fold.

Numerical Results

Figure 2B:
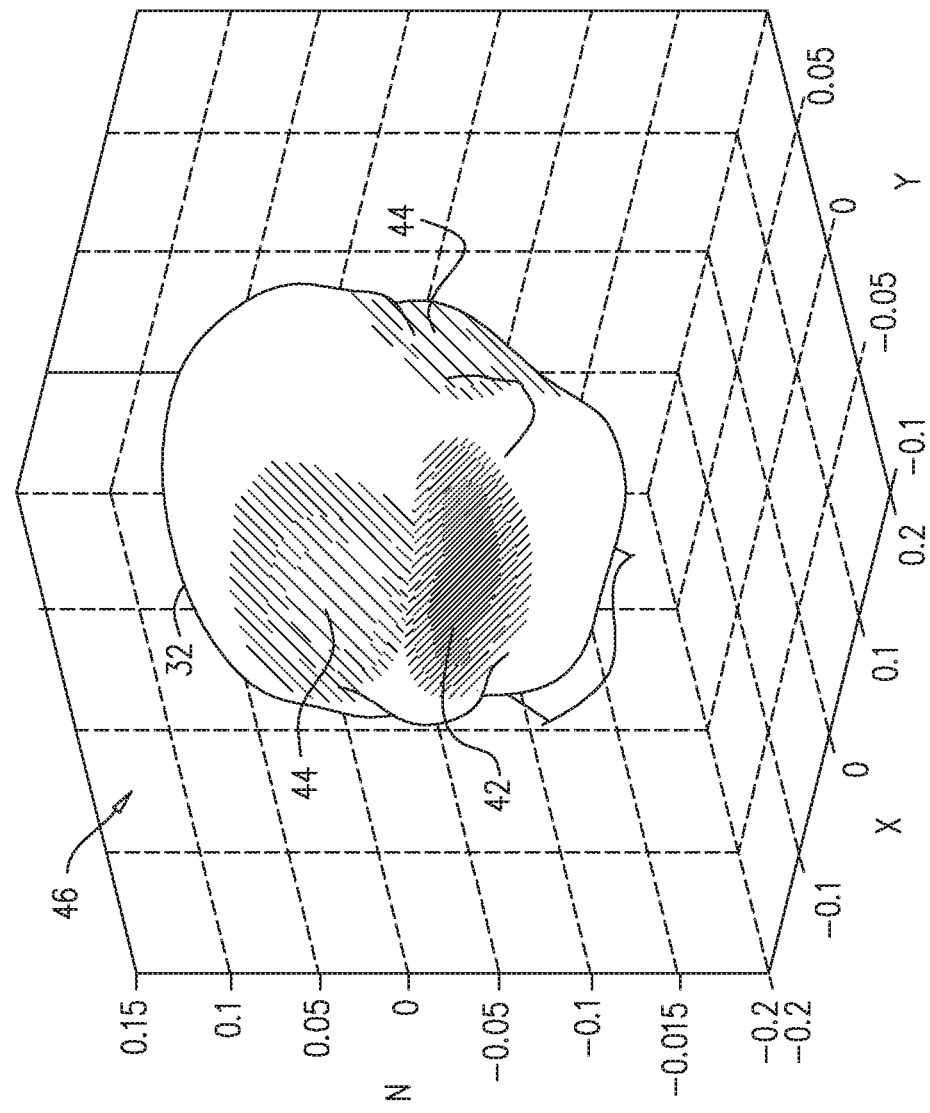

FIGS. 2A and 2B are schematic maps 40 and 46 of vibroEEG signals due to acoustic stimulation at two different locations within the brain, in accordance with an embodiment of the invention. The maps were computed using the Brainstorm analysis toolbox, as described by Tadel et al., in "Brainstorm: a user-friendly application for MEG/EEG analysis," *Computational intelligence and neuroscience* 2011 (2011), ID 879716. In both maps 40 and 46, a unit current dipole, oriented in the y-direction, was moved by 1 mm in the z-direction inside head 32. In FIG. 2A the dipole was located close to the skull, whereas in FIG. 2B the dipole was deep inside the cortex.

The result in both of maps 40 and 46 was a current quadrupole field, with positive-potential lobes 42 and negative-potential lobes 44. The shapes and locations of lobes 42 and 44 map back in each case to the dipole location. Because the quadrupole field is twice as sharp spatially as the dipole field, measurement of the quadrupole field gives a more accurate indication of the location of the moving dipole. The field of the shallow dipole in map 40, however, is still substantially sharper than that of the deep dipole in map 44.

Figure 3A:
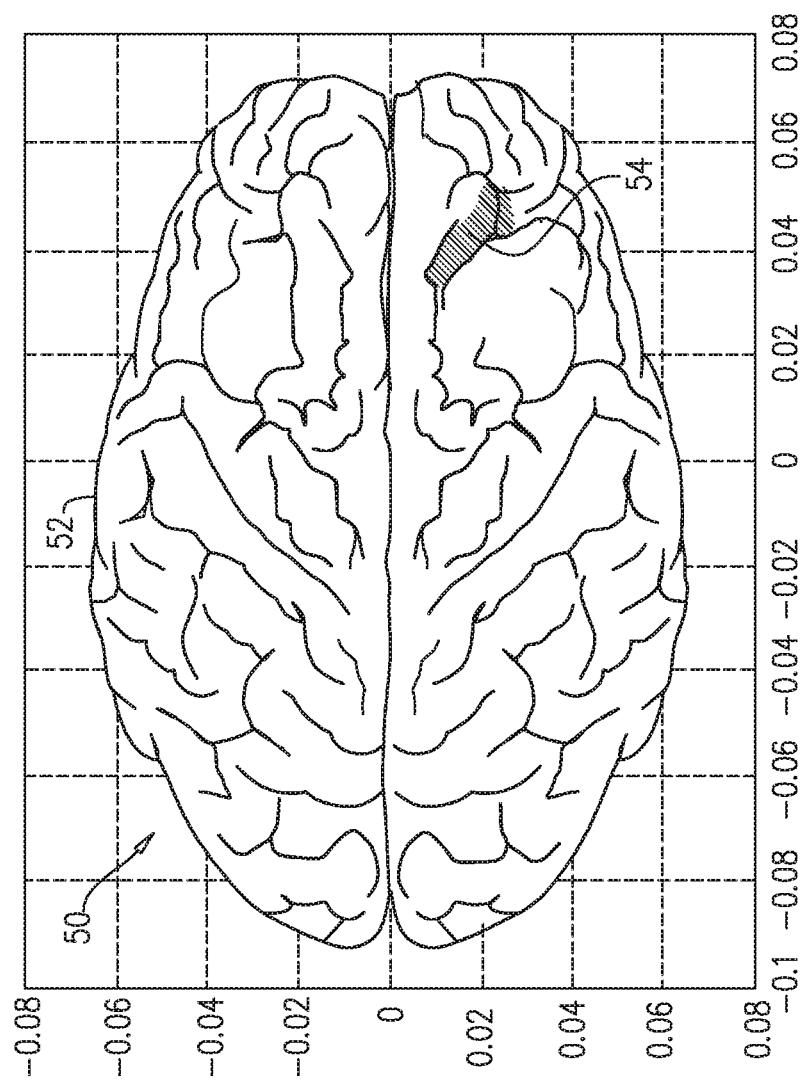

FIGS. 3A and 3B are schematic maps 50 and 56 of vibroEEG signals due to acoustic stimulation of two different vibrational modes in a brain 52, in accordance with another embodiment of the invention. These maps illustrate how different vibrational modes can be used to stimulate and isolate the vibroEEG contributions of different sulci 54 and 58 in brain 52. Because of the short Euclidean distance between these sulci, their respective contributions to conventional EEG signals cannot readily be separated.

To construct maps 50 and 56, the vibrational response of the brain was calculated using the above-mentioned Brainstorm model, and singular value decomposition (SVD) was applied in order to find the vibrational resonant modes. The maps show the computed amplitude of vibration, and hence the strength of the resulting vibroEEG signal, in two different vibrational modes, with different frequencies, with heavier shading in the areas of the most intense vibration. Thus, in map 50, the vibroEEG signal originates primarily from a first sulcus 54, whereas in map 56, the vibroEEG signal at a different frequency originates from a neighboring sulcus 58. Console 34 can use this distinction in separating the EEG signals arising from mutually-adjacent locations on different sulci of the brain, which are excited by different vibrational modes.

Method of Operation

Figure 4:
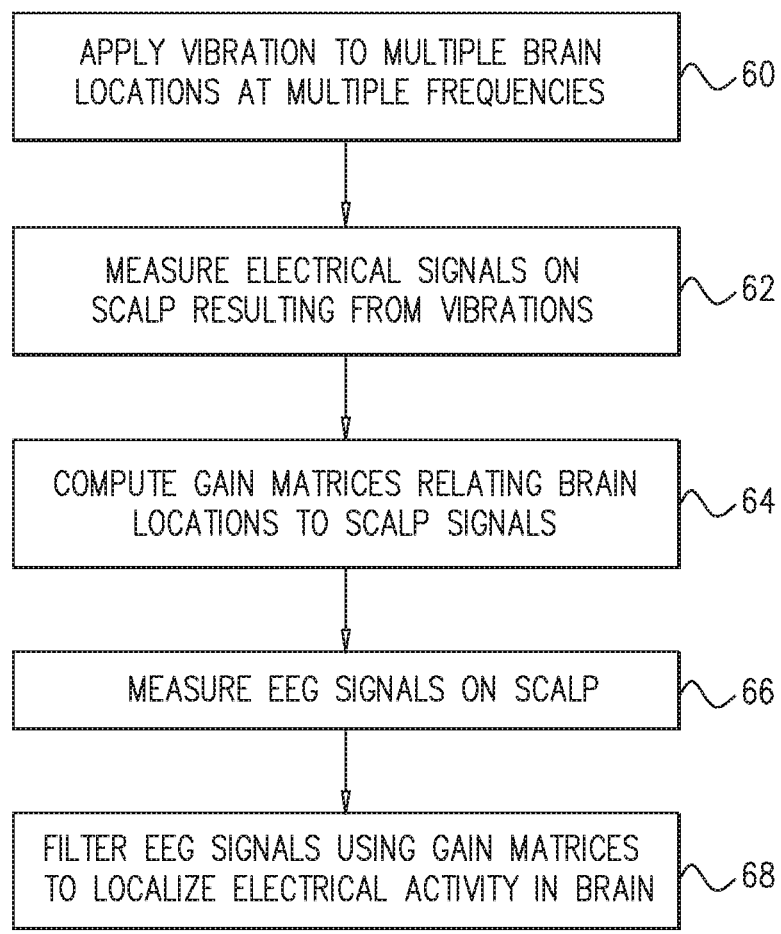
FIG. 4 is a flow chart that schematically illustrates a method for EEG measurement and localization, in accordance with an embodiment of the invention.

FIG. 4 is a flow chart, which schematically illustrates a method for EEG measurement and localization, in accordance with an embodiment of the invention. The method is described, for the sake of clarity and concreteness, with reference to the components of system 20, as shown in FIG. 1. Alternatively, however, the principles of the present embodiment may be applied, mutatis mutandis, in other system environments having appropriate facilities for applying vibrational stimulation to and measuring electrical signals from the brain.

Ultrasonic generator 22 drives transducers 24 and 26 to apply vibrations to locations in the brain, at an acoustic stimulation step 60. As explained early, vibrations can advantageously be applied by driving transducers 24 and 26 at different, respective ultrasonic frequencies, thus causing the brain tissue to vibrate at a frequency equal to the difference between the driving frequencies. Multiple different vibrational frequencies can be probed in this manner, by varying one or both of the ultrasonic frequencies.

Furthermore, by focusing the ultrasonic beams from transducers 24 and 26 to overlap at a given location within the brain, the specific vibrational response of that location can be probed. The foci of the ultrasonic beams can be scanned over the volume of the brain in order to measure the responses of different locations. Alternatively, vibrations can be applied over a wider area, as the differences in resonant vibrational response of different regions of the brain (as illustrated, for example, in FIG. 3A/B) can be used to enhance the spatial resolution of vibroEEG measurements.

While ultrasonic generator 22 applies the vibrations to the brain at step 60, EEG front end 28 receives electrical signals from electrodes 30, at a vibroEEG measurement step 62. Console 34 filters the signals to extract the components at the present frequency of vibration. This is the electrical signal that originates from the vibrational motion of the dipoles at the location that is currently being stimulated and thus gives an accurate indication of the relation between the electrical activity within the brain at this location and the potentials measured by electrodes 30.

Console 34 processes the vibroEEG signals measured at step 62 in order to estimate a respective gain matrix for each stimulation frequency and/or each stimulated location in the brain, at a gain matrix computation step. (The gain matrix is only "estimated," because the actual amplitude of the signal on the cortex cannot be measured directly.) As explained earlier, each of these gain matrices relates the local electrical activity in the brain stimulated at step 60 to the resulting vibroEEG potentials that were measured at the locations of electrodes 30 on the scalp. Multiple gain matrices are concatenated to produce a matrix of a rank that is equal to or greater than the rank of the vector X of distinct signal sources that are to be resolved.

Alternatively or additionally, the vibroEEG gain matrix can be calculated theoretically from a volumetric image of the brain, such as an image produced by an MRI scan of the subject. Although the model can be imprecise, the ability of system 20 to induce localized vibrations makes it possible to essentially probe the brain's electrical activity in different points of the brain.

To localize and map intrinsic electrical activity of the brain, console 34 measures EEG signals collected by front end 28 from electrodes 30, at an EEG measurement step 66. These signals are typically collected in the absence of vibrational stimulation. Alternatively, assuming the vibrational stimulation applied at step 60 to be in a range above 100 Hz, console 34 can measure the intrinsic EEG signals simultaneously with the vibroEEG measurement of step 62 by applying a low-pass filter to the measured signals.

Console 34 applies the gain matrices derived at step 64 in filtering the EEG signals measured at step 66, at an EEG filtering step 68. For this purpose, for example, console 34 inverts the concatenated gain matrix, using methods of matrix inversion that are known in the art. The inverted gain matrix can then be multiplied by the matrix of measured EEG signal values produced at step 66 in order to reconstruct an estimated vector $\tilde{X}$ of electrical sources at respective locations in the brain for any given EEG signal component. Console 34 can thus construct a map of the brain electrical activity over the multiple different locations using the gain matrices. The map may be presented on display 36, as noted above.

Figure 5:
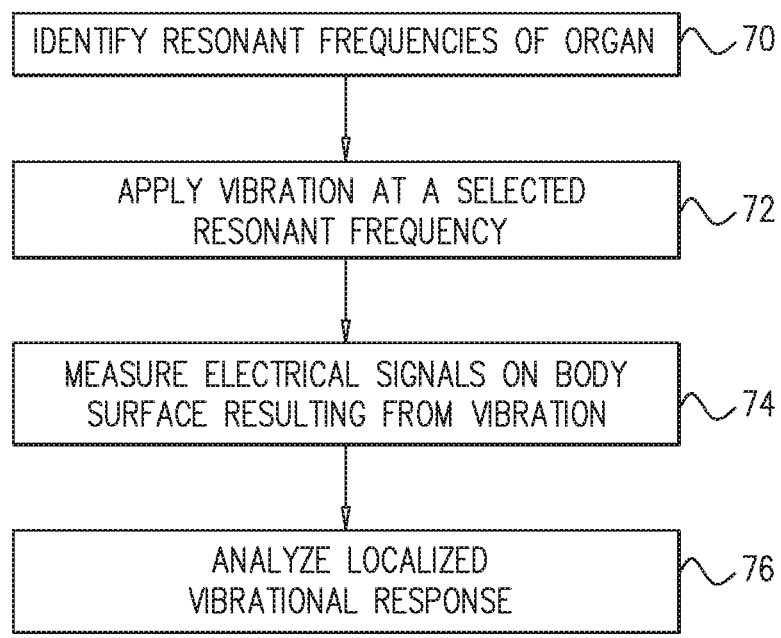
FIG. 5 is a flow chart that schematically illustrates a method for analyzing localized electrical activity in body organs, in accordance with an embodiment of the invention.

FIG. 5 is a flow chart that schematically illustrates a method for analyzing localized electrical activity in body organs, in accordance with an embodiment of the invention.

Although the preceding embodiments are described with specific reference to stimulating and measuring electrical activity in the brain, the principles of these and the present embodiment are also applicable, mutatis mutandis, to other organs, such as the heart.

As an initial step 70, console 34 identifies one or more resonant frequencies of vibration of a part of the organ of interest. The resonant frequencies can be identified, for example, by processing a volumetric image (such as an MRI scan) of the organ in order to estimate its frequency response, as explained above. Alternatively or additionally, one or more of transducers 24 and 26 can be actuated to apply acoustic energy to the body at multiple different frequencies, and the acoustic and/or electrical response of the organ can be measured in order to identify a resonant response.

Alternatively, the vibrational modes can be measured by methods of magnetic resonance elastography that are known in the art, as described, for example, by Mariappan et al., in "Magnetic resonance elastography: a review," *Clinical anatomy* 23 (2010), pages 497-511, which is incorporated herein by reference.

Console 34 actuates transducers 24 and 26, as explained above, so as to apply acoustic energy at the identified resonant frequency to the body in the vicinity of the organ, at a vibration application step 72. Console 34 measures electrical signals resulting from the vibration in response to the applied acoustic energy at one or more positions on a surface of the body, at an electrical measurement step 74. Typically, these signals are collected from electrodes on the body surface in proximity to the organ of interest (for example, electrodes 30). Console 34 may filter the signals in order to extract the electrical activity at the resonant frequency of vibration.

Console 34 processes the electrical signals measured at step 74 in order to analyze the localized vibrational response of the organ, at an analysis step 76. Applying vibrations to multiple different locations within the organ, and wherein measuring the electrical signals comprises constructing a map of electrical activity over the multiple different locations. For this purpose, console 34 may have driven the transducers at step 72 to excite multiple different vibrational modes in different locations in the organ. For example, in the brain, the console can distinguish between the electrical signals arising from mutually-adjacent locations on different sulci of the brain, which are excited by different vibrational modes, as illustrated above in FIG. 3A/B. Although it can be useful to focus the acoustic excitation applied at step 72, this sort of resonant response makes it possible to localize vibrations even when only a single, non-directional transducer is used.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:
1. A diagnostic method, comprising:
applying a vibration at a selected frequency to a location within a brain of a living subject;
measuring electrical signals resulting from the vibration at multiple positions on a scalp of the subject;

processing the measured electrical signals in order to compute an electrical gain matrix between the location within the brain and the positions on the scalp;

measuring electroencephalogram (EEG) signals at the multiple positions on the scalp; and filtering the EEG signals using the gain matrix in order to identify brain electrical activity originating from the location.

2. The method according to claim 1, wherein measuring the electrical signals comprises extracting the electrical signals at the frequency of the vibration.

3. The method according to claim 2, wherein the frequency of the vibration is in a first range between 100 Hz and 10,000 Hz, while the EEG signals are measured in a second range, which is below 100 Hz.

4. The method according to claim 1, wherein applying the vibration comprises applying vibrations to multiple different locations within the brain, in order to compute respective gain matrices for the locations, and wherein filtering the EEG signals comprises constructing a map of the brain electrical activity over the multiple different locations using the gain matrices.

5. The method according to claim 1, wherein applying the vibration comprises applying vibrations at multiple different frequencies so as to excite multiple different vibrational modes in different locations in the brain, and wherein processing the measured electrical signals comprises computing respective electrical gain matrices corresponding to the different vibrational modes.

6. The method according to claim 5, wherein filtering the EEG signals comprises distinguishing between the EEG signals arising from mutually-adjacent locations on different sulci of the brain, which are excited by different ones of the vibrational modes.

7. The method according to claim 5, wherein filtering the EEG signals comprises concatenating the electrical gain matrices to produce a combined gain matrix, inverting the combined gain matrix, and applying the inverted gain matrix to the EEG signals in order to reconstruct the electrical activity in the brain.

8. The method according to claim 1, wherein applying the vibration comprises directing ultrasonic waves toward the brain at different, first and second ultrasonic frequencies, which are separated by a frequency difference equal to the selected frequency of the vibration.

9. The method according to claim 8, wherein applying the vibration comprises focusing the ultrasonic waves onto the location within the brain.

10. A diagnostic system, comprising:

one or more acoustic transducers, which are configured to apply a vibration at a selected frequency to a location within a brain of a living subject;

an array of electrodes, which are configured to measure electrical signals resulting from the vibration at multiple positions on a scalp of the subject and to measure electroencephalogram (EEG) signals at the multiple positions on the scalp; and a console, which is configured to process the measured electrical signals in order to compute an electrical gain matrix between the location within the brain and the positions on the scalp, and to filter the EEG signals using the gain matrix in order to identify brain electrical activity originating from the location.

11. The system according to claim 10, wherein the console is configured to extract the electrical signals at the frequency of the vibration and to apply the extracted electrical signals in computing the electrical gain matrix.

12. The system according to claim 10, wherein the one or more acoustic transducers are configured to apply vibrations to multiple different locations within the brain, and the console is configured to compute respective gain matrices for the locations, and to construct a map of the brain electrical activity over the multiple different locations using the gain matrices.

13. The system according to claim 10, wherein the one or more acoustic transducers are configured to apply vibrations at multiple different frequencies so as to excite multiple different vibrational modes in different locations in the brain, and the console is configured to compute respective electrical gain matrices corresponding to the different vibrational modes.

14. The system according to claim 10, wherein the one or more acoustic transducers are configured to direct ultrasonic waves toward the brain at different, first and second ultrasonic frequencies, which are separated by a frequency difference equal to the selected frequency of the vibration.

15. A diagnostic method, comprising:

identifying a resonant frequency of vibration of a part of an organ in a body of a living subject;

applying acoustic energy at the identified resonant frequency to the body in a vicinity of the organ; and measuring a characteristic of electrical signals resulting from the vibration in response to the applied acoustic energy at one or more positions on a surface of the body.

16. The method according to claim 15, wherein identifying the resonant frequency comprises processing a volumetric image of the organ in order to estimate a frequency response of the organ.

17. The method according to claim 15, wherein identifying the resonant frequency comprises measuring the resonant frequency using magnetic resonance elastography.

18. The method according to claim 15, wherein identifying the resonant frequency comprises applying the acoustic energy to the body at multiple different frequencies, and measuring a response of the organ so as to identify a resonant response.

19. The method according to claim 15, wherein measuring the characteristic of the electrical signals comprises extracting the electrical signals at the resonant frequency of the vibration.

20. The method according to claim 19, wherein extracting the electrical signals comprises measuring the electrical signals in a combination of resonant modes.

21. The method according to claim 15, wherein applying the acoustic energy comprises applying vibrations to multiple different locations within the organ, and wherein measuring the characteristic of the electrical signals comprises constructing a map of electrical activity over the multiple different locations.

22. The method according to claim 21, wherein applying the vibrations comprises exciting multiple different vibrational modes in different locations in the organ.

23. The method according to claim 22, wherein the organ is the brain, and wherein constructing the map comprises distinguishing between the electrical signals arising from mutually-adjacent locations on different sulci of the brain, which are excited by different ones of the vibrational modes.

24. The method according to claim 15, wherein applying the acoustic energy comprises directing ultrasonic waves toward the organ at different, first and second ultrasonic frequencies, which are separated by a frequency difference equal to the identified resonant frequency.

25. The method according to claim 24, wherein directing the ultrasonic waves comprises focusing the ultrasonic waves onto the part of the organ.

* * * * *